(12) United States Patent
Lewis et al.

(10) Patent No.: US 7,864,316 B2
(45) Date of Patent: Jan. 4, 2011

(54) SPECTROMETRIC CHARACTERIZATION OF PHARMACEUTICAL HETEROGENEITY

(75) Inventors: E. Neil Lewis, Olney, MD (US);
Kenneth S. Haber, Frederick, MD (US)

(73) Assignee: Malvern Instruments, Ltd., Malvern (GB)

( * ) Notice: Subject to any disclaimer, the term of this patent is extended or adjusted under 35 U.S.C. 154(b) by 287 days.

(21) Appl. No.: 11/986,548

(22) Filed: Nov. 20, 2007

(65) Prior Publication Data

US 2009/0086200 A1    Apr. 2, 2009

Related U.S. Application Data

(60) Provisional application No. 60/993,141, filed on Sep. 10, 2007, provisional application No. 60/860,345, filed on Nov. 20, 2006.

(51) Int. Cl.
*G01J 3/28* (2006.01)
(52) U.S. Cl. ............................ 356/326; 356/300; 356/72
(58) Field of Classification Search ................. 356/326, 356/300, 72
See application file for complete search history.

(56) References Cited

U.S. PATENT DOCUMENTS

| 6,490,035 | B1 * | 12/2002 | Folestad et al. | ............. 356/319 |
| 6,517,230 | B1 * | 2/2003 | Afnan et al. | ................ 366/142 |
| 7,075,645 | B2 * | 7/2006 | Gehrlein et al. | ............. 356/328 |
| 2004/0019462 | A1 | 1/2004 | Gehrlein et al. | |
| 2004/0057650 | A1 | 3/2004 | Folestad | |

FOREIGN PATENT DOCUMENTS

WO    WO 02/18912    *    3/2002

* cited by examiner

*Primary Examiner*—L. G Lauchman
(74) *Attorney, Agent, or Firm*—Kristofer E. Elbing

(57) ABSTRACT

In one general aspect, a spectroscopic method for monitoring heterogeneity of a sample is disclosed. In this method, sampled spectroscopic measurements are acquired over a range of different micro locations in a macro-sample of the sample. This step is repeated for micro-locations in further macro-samples of the sample, and a statistical measure of chemical heterogeneity is derived from the acquisitions. In another general aspect, differently sized samples are acquired, and a statistical measure of chemical heterogeneity is derived from these acquisitions.

26 Claims, 7 Drawing Sheets

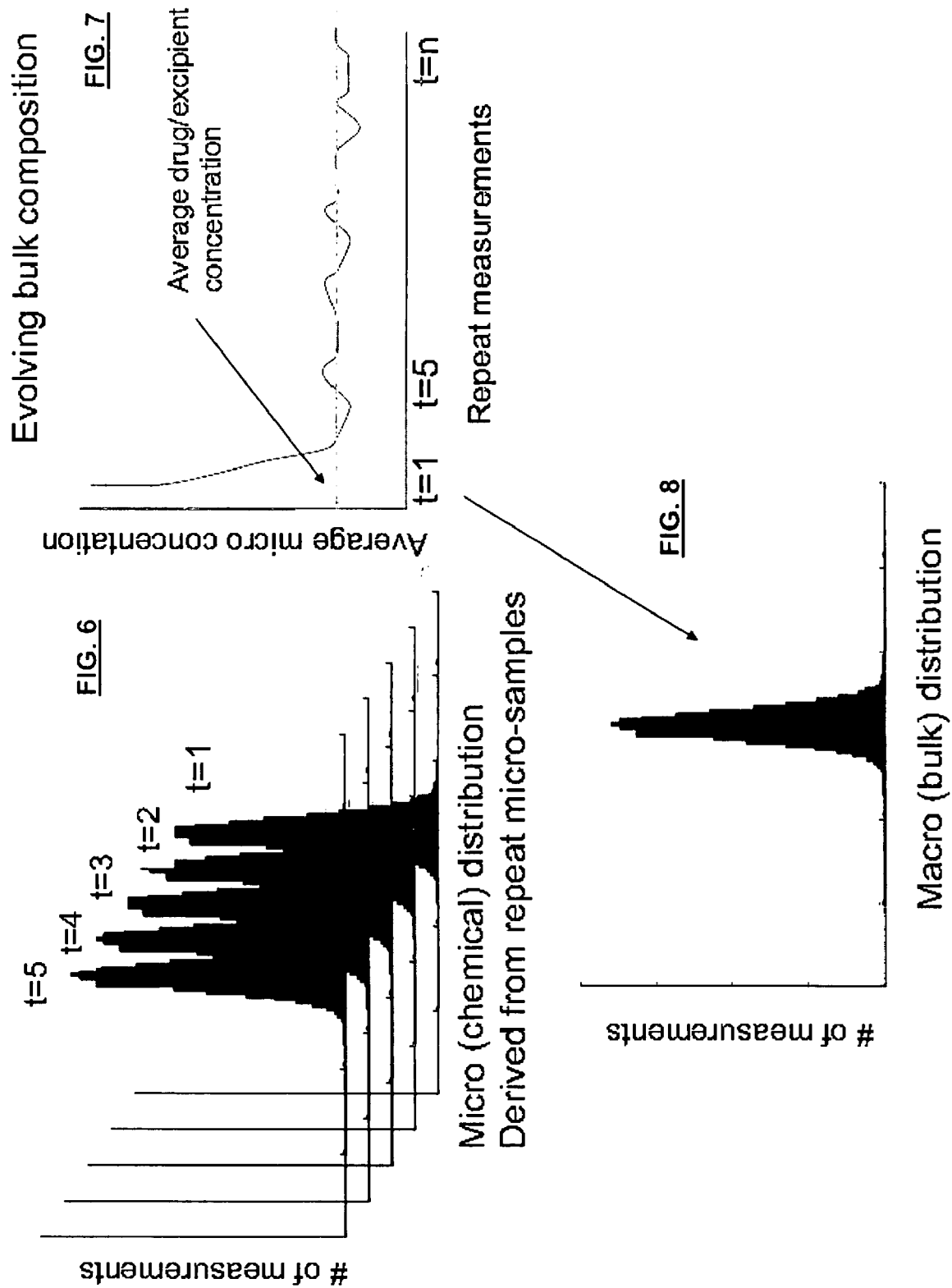

SPECTROMETRIC CHARACTERIZATION OF PHARMACEUTICAL HETEROGENEITY

CROSS-REFERENCE TO RELATED APPLICATIONS

This application claims the benefit under 35 U.S.C. 119(e) of U.S. Provisional Application No. 60/860,345, filed on Nov. 20, 2006, and Provisional Application No. 60/993,141, filed on Sep. 10, 2007. These applications are both herein incorporated by reference.

FIELD OF THE INVENTION

This invention pertains to spectrometric instruments, such as spectrometric instruments for characterizing pharmaceutical heterogeneity.

BACKGROUND OF THE INVENTION

Spectrometric techniques have been applied to monitoring mixing processes, such as the mixing of pharmaceutical blends. One approach has been to take a series of single spectra of a blend through a window in a mixing vessel. Mixing can then be carried out until this single measurement reaches an end point. This method is simple to implement, but it provides the user with relatively little information about the distribution of components of the mixture.

Another approach has been to acquire a series of near-infrared chemical images of a blend in a mixing vessel. These images can then be analyzed to derive statistical properties, such as the mean, standard deviation, kurtosis, or skew of the distribution, as described in more detail in published U.S. application No. US2004-0211861, which is herein incorporated by reference. This approach can provide more information about the distribution of mixture components than does the single-measurement approach, but it can be relatively expensive to implement.

SUMMARY OF THE INVENTION

In one general aspect, the invention relates to a spectroscopic method for monitoring heterogeneity of a sample. The method includes acquiring sampled spectroscopic measurements distributed over a range of different micro locations in a macro-sample of the sample, repeating the step of acquiring for each of a plurality of micro-locations in each of further macro-samples of the sample, and deriving from the sampled spectroscopic measurements acquired in the steps of acquiring a statistical measure of chemical heterogeneity.

In preferred embodiments, the steps of acquiring can be performed for a pharmaceutical mixture during a blending process. The blending process can be intermittent with each of the macro-samples being an exposed area of the pharmaceutical that is presented during a pause in the blending process. The steps of acquiring can be performed for pharmaceutical dosage units. Each of the steps of acquiring can be performed for a different one of the plurality of dosage units. The step of acquiring can operate on light brought from micro-samples through a plurality of optical channels. The optical channels can be optical fibers. The step of acquiring can operate on light brought from the micro-locations to a set of detectors. The steps of acquiring can be performed using at least one moving mirror. The size of the micro-samples can be on the order of the milled ingredient size for a pharmaceutical mixture. The size of the micro-samples can be on the order of the domain sizes of individual species in a pharmaceutical mixture. The size of the micro-samples can be on the order of 10 microns. The size of the micro-samples can be on the order of 125 microns. The macro-samples can be taken for a part of the surface area of the sample. The sampled spectroscopic measurements can be acquired from different vantage points. The sample can be moved relative to a detector to cause the sampled spectroscopic measurements to be acquired from different locations. The steps of acquiring and repeating can employ differently sized micro locations. The differently sized micro locations can be concentric.

In another general aspect, the invention features a spectroscopic apparatus for monitoring heterogeneity of a sample. The apparatus includes a sampling detector operative to acquire sampled spectroscopic measurements distributed over a range of different micro locations in a macro-sample of the sample, a sequencer operative to cause the sampling detector to repeatedly acquire samples for each of a plurality of micro-locations in each of a plurality of macro-samples of the sample, and a spectral processor operative to derive from the sampled spectroscopic measurements a statistical measure of chemical heterogeneity.

In a further general aspect, the invention features a spectroscopic apparatus for monitoring heterogeneity of a sample that includes means for acquiring sampled spectroscopic measurements distributed over a range of different micro locations in a macro-sample of the sample, means for causing the sampling detector to repeatedly acquire samples for each of a plurality of micro-locations in each of a plurality of macro-samples of the sample, and means for deriving from the sampled spectroscopic measurements a statistical measure of chemical heterogeneity.

In another general aspect, the invention features a spectroscopic method for monitoring heterogeneity of a sample that includes acquiring a first sampled spectroscopic measurement of a first size in a sample of the sample, acquiring a second sampled spectroscopic measurement of a second size in a sample of the sample, wherein the first and second measurements are of the same type, and deriving from the sampled spectroscopic measurements acquired in the steps of acquiring a measure of chemical heterogeneity.

In preferred embodiments, the method can further include a step of adjusting a lens to adjust the size of the sampled micro location. The step of acquiring a first sample and the step of acquiring a second sample can acquire samples that are concentric. The step of acquiring a first sample and the step of acquiring a second sample can be performed for a pharmaceutical mixture. The steps of acquiring can be performed for a pharmaceutical mixture during a blending process. The steps of acquiring can be performed for pharmaceutical dosage units. Each of the steps of acquiring can be performed for a different one of the plurality of dosage units. The step of acquiring can operate on light brought from micro-samples through one or more optical channels. The optical channels can be optical fibers. The step of acquiring can operate on light brought from the sample to a set of detectors. The steps of acquiring can be performed using at least one moving mirror. The size of at least one of the sample measurements can be on the order of the milled ingredient size for a pharmaceutical mixture. The size of at least one of the sampled measurements can be on the order of the domain sizes of individual species in a pharmaceutical mixture. The size of at least one of the sampled measurements can be on the order of 10 microns. The size of at least one of the sampled measurements can be on the order of 125 microns. The sampled measurements can be acquired from different vantage points. The sample can be moved relative to a detector to cause the sampled spectroscopic measurements to be acquired from different locations.

In a further general aspect, the invention features a spectroscopic apparatus for monitoring heterogeneity of a sample that includes one or more sampling detectors operative to acquire spectroscopic measurements from the sample, means for causing the one or more sampling detectors to acquire a first sampled spectroscopic measurement of a first size in a sample of the sample, and a second sampled spectroscopic measurement of a second size in a sample of the sample, wherein the first and second measurements are of the same type, and a spectral processor operative to derive from the sampled spectroscopic measurements a statistical measure of chemical heterogeneity. In preferred embodiments, the means for causing can include an adjustable lens.

Systems according to the invention can derive important blend statistics using relatively simple and inexpensive measurement apparatus. This can allow a pharmaceutical manufacturer to obtain detailed information about the uniformity of its pharmaceutical mixtures, and therefore potentially increase the safety and/or efficacy of its drugs. And because this can be accomplished without requiring a relatively expensive imaging instrument, these improvements can be accomplished at a lesser cost.

Systems according to the invention can also be less expensive because they can employ a more tolerant optical front end than is typically provided in an imaging system. Small misalignments can be less important where the acquired spectral information does not need to be assembled into an image. Alignment or focus changes as a result of mechanical motion or vibration may similarly only result in some averaging in the micro-samples, and this averaging may even be beneficial in certain circumstances.

BRIEF DESCRIPTION OF THE DRAWINGS

FIG. 6 is a series of micro distribution plots for a series of samples for the system of FIG. 1;

FIG. 7 is a plot of average concentration for the samples shown in FIG. 6;

FIG. 8 is a plot of macro distribution for the samples shown in FIG. 6;

DESCRIPTION OF AN ILLUSTRATIVE EMBODIMENT

Figure 1:
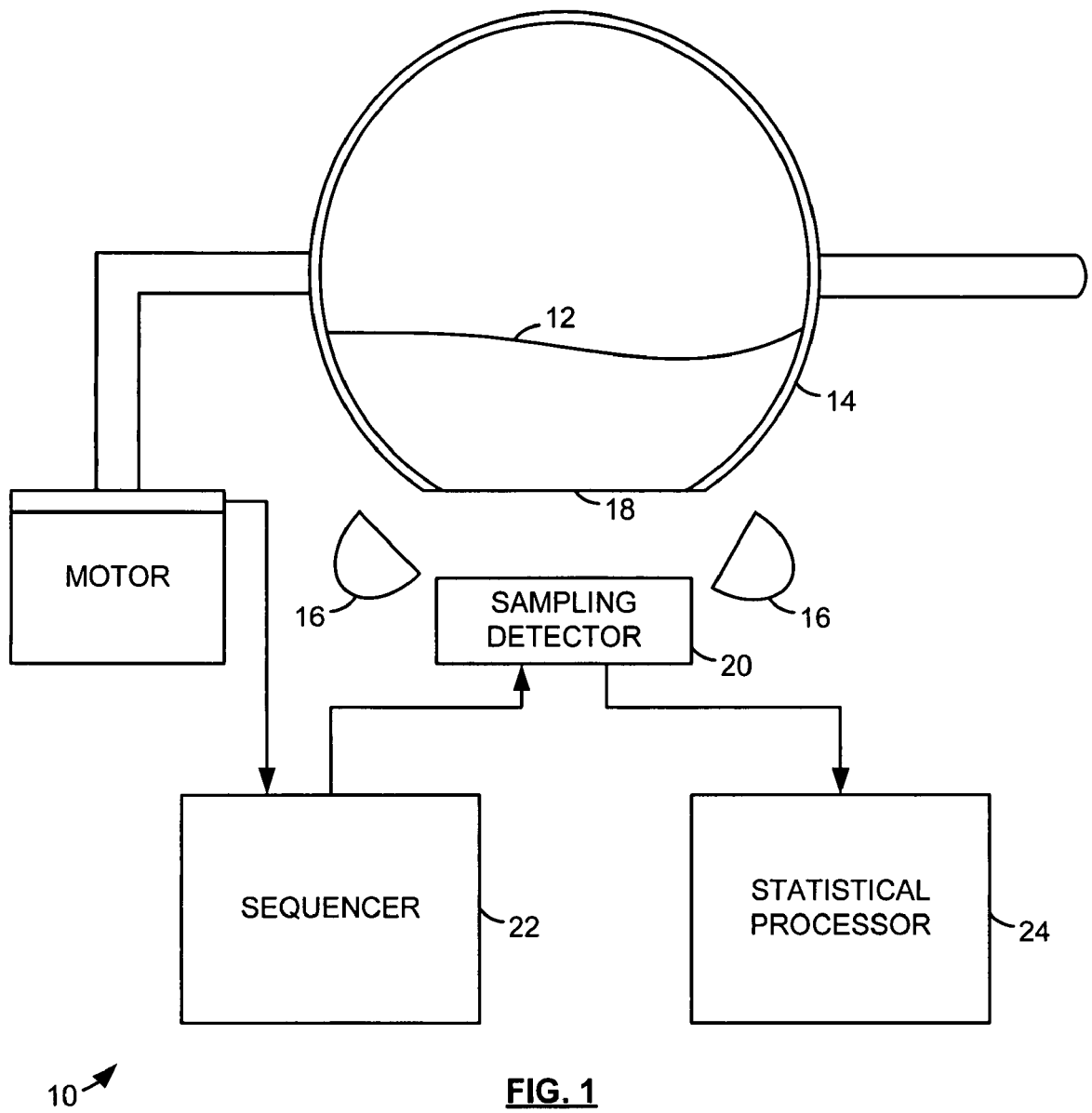
FIG. 1 is a diagram of an illustrative embodiment of a spectrometric pharmaceutical heterogeneity characterization system according to the invention.

Referring to FIG. 1, an illustrative system 10 according to the invention is designed to characterize the mixing of a pharmaceutical powder blend 12 in a motor-driven mixing vessel 14, such as a V-blender. Other types of processing devices could also be accommodated, however, such as hoppers or granulators. And other types of pharmaceutical mixtures or dosage units can be characterized, such as solid dosage forms (e.g., capsules or tablets), suspensions, or even mixtures of immiscible fluids.

The system 10 includes one or more infrared illumination sources 16 directed toward a window 18 in the mixing vessel 14. One or more sampling detectors 20 are positioned near the vessel in such a way that they can acquire spectrometric samples through the window. A sequencer 22 can trigger acquisitions by the sampling detector, and a statistical processor 24 can receive the acquired samples.

Figure 2:
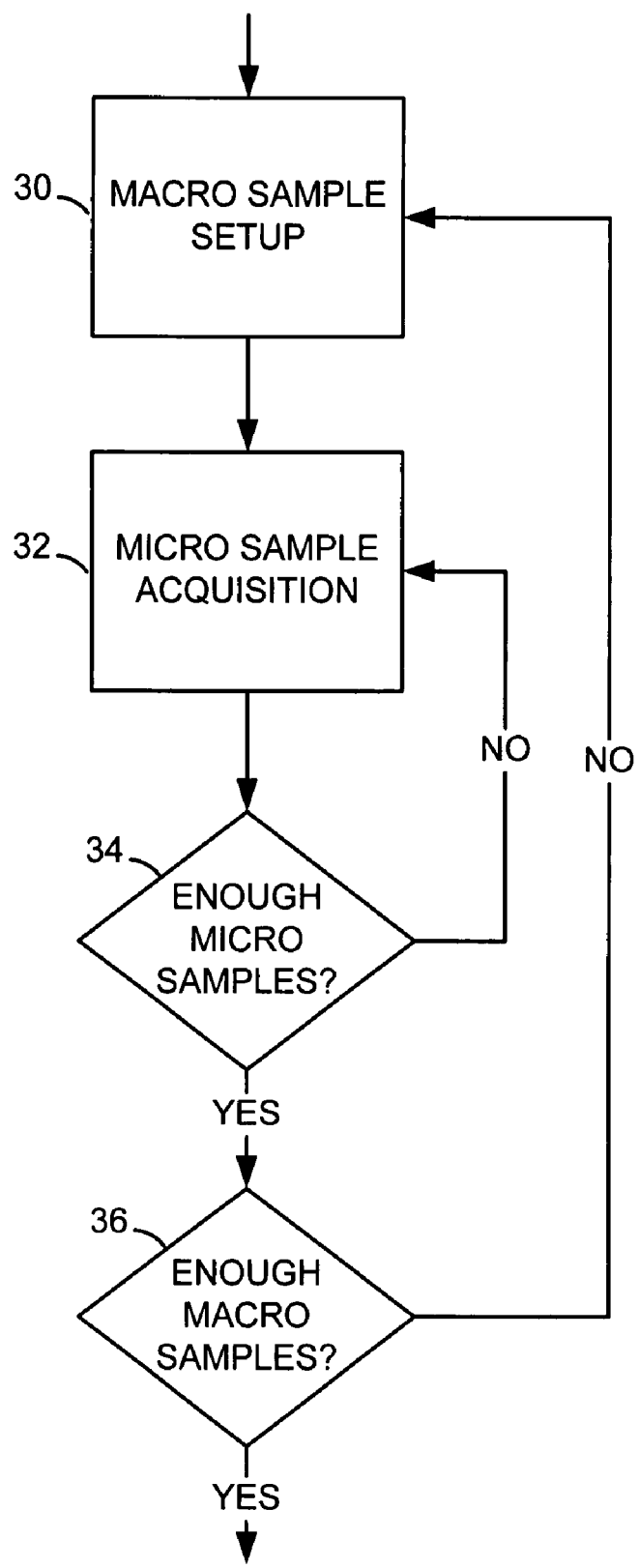
FIG. 2 is a flowchart illustrating the operation of the system of FIG. 1.

Referring also to FIG. 2, the system 10 is first put in an initial macro-sampling state (step 30). In the illustrative embodiment, this state is one where the blender window 18 is in front of the sampling detector 20. The system then performs a series of micro-sample acquisitions (step 32). Once the micro-sampling is complete (step 34), the system mixes the blend until another macro-sampling state is reached, and the system begins another series of micro-sampling acquisitions.

The acquisition process ends at the end of a final macro-sample (step 36). This can be the last of a predetermined number of macro-samples in a fixed sampling schedule. The system can also stop the process for other reasons, such as once certain predetermined mixing characteristics have been achieved, or when an error condition is detected.

Figure 3A:
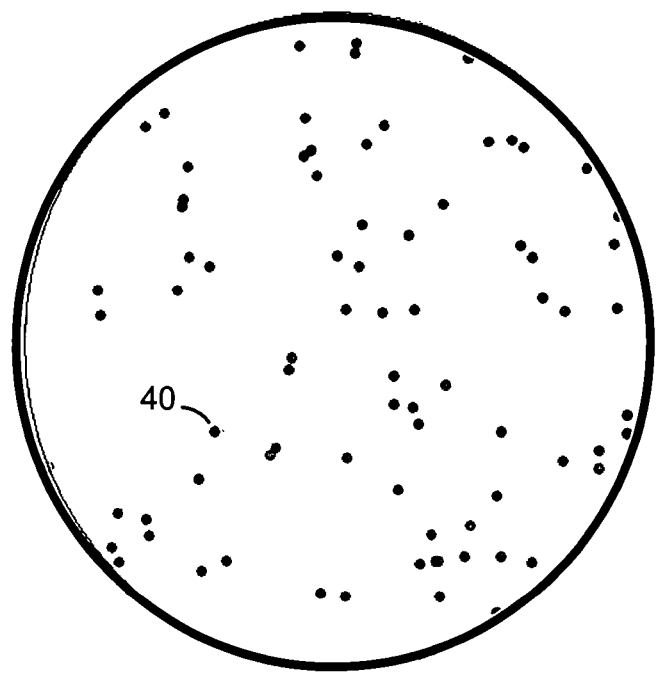
FIG. 3A is a first illustrative sampling map for the system of FIG. 1.
Figure 3B:
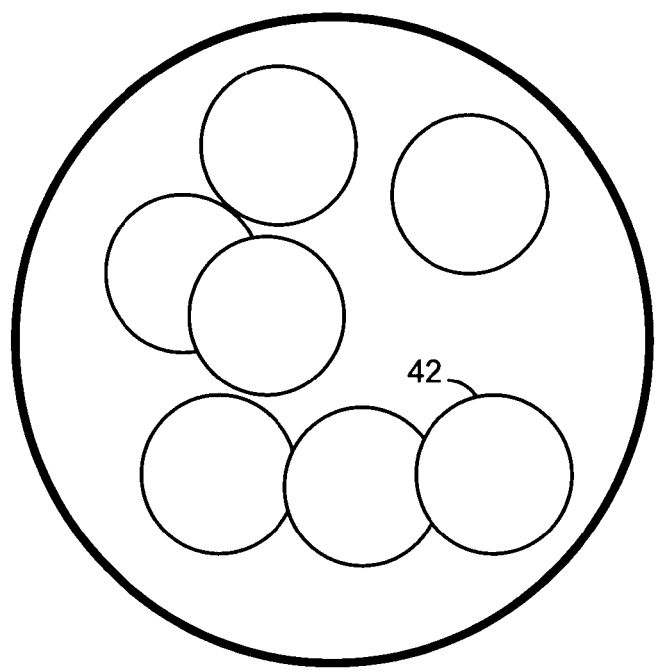
FIG. 3B is a second illustrative sampling map for the system of FIG. 1.

Referring also to FIG. 3A-3B, the sampling detector is designed to acquire a number of micro-samples at different locations in the sample during each macro-sample period. The system can use one or more different types of sampling patterns, such as random patterns of non-overlapping samples 40 or overlapping samples 42. The sequencing of the acquisition of the samples is generally defined by the nature of the detector and its sequencer.

Figure 4:
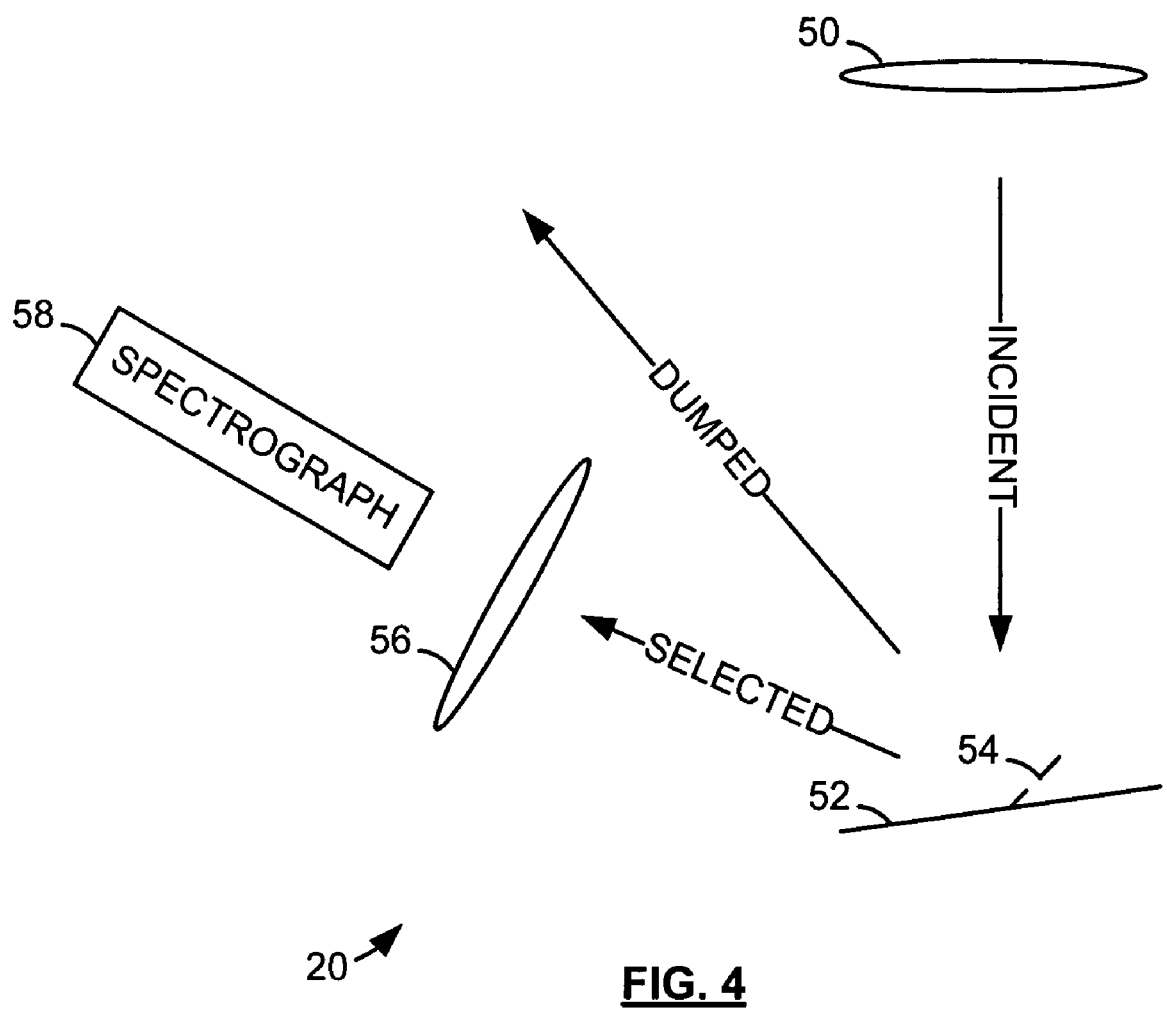
FIG. 4 is a diagram of a scanning-mirror implementation of a detector element for the system of FIG. 1.

Referring also to FIG. 4, one possible implementation of the sampling detector 20 that can perform the micro-sampling operations is based on a micromirror array. In this implementation, lamps at an oblique angle are used to illuminate the entire sampled area. A collection lens 26 images the sampled area onto a micromirror array 52, oriented so that in one state the mirrors reflect the incident light into a beam dump. In the other state the mirrors (see 54) reflect the light into a lens 56 which images the micromirror array onto the slit of a spectrograph 58 equipped with a diode array detector. Alternatively, the aperture may be imaged onto the round face of a fiber bundle, which is round on one end and linear on the other end, with the linear end serving as the slit for the spectrograph.

In a second implementation the illumination is as above, but an optical system which includes a scanning mirror images a portion of the illuminated area onto an aperture. This aperture is then imaged onto the slit of the spectrograph or onto a fiber bundle as described above. The spatial resolution is determined by the size of the aperture projected through the collection optics onto the sample. The aperture may consist of an iris, slit, wedge or a small mirror, positioned to pick off only a small portion of the sample image.

In a third implementation the oblique illumination is provided by the modulated light from a Fourier Transform (FT) interferometer, and the micromirror array selectively images a portion of the illuminated area directly into a single element detector.

In a fourth implementation the illumination is the modulated light from an FT interferometer, and an optical system which includes a scanning mirror images a portion of the illuminated area onto an aperture which is imaged directly onto a detector.

In a fifth implementation a beamsplitter is used to couple a collimated broadband beam into the collection path. The light is telescoped down and sent through an aperture, which is imaged to a spot on the sample by an optical system which incorporates a scanning mirror. Light from that spot follows the same path back to the beamsplitter and is then focused onto the slit of a spectrograph.

As before, the collimated broadband illumination source can be the modulated output of a Michelson interferometer, in which case the spectrograph is replaced by a single element detector.

Instead of telescoping the illumination beam to the size of a small aperture, the entire collimated excitation beam can illuminate a micromirror array oriented so that an mirror in the 'on' state will direct a portion of the collimated incident beam to a corresponding spot on the sample, and the reflected light from that spot will be directed to the beamsplitter and then to either the slit of the spectrograph or into a detector in the case of FT illumination. The spot could also be brought to the sample through the use of an optical microscope.

In still another configuration, a spectrograph (or a detector for the case of FT modulated illumination) can be set up to collect light from a large area, and a small portion of that area can be illuminated oblique to the collection angle, either using a micromirror array or by again making use of the small aperture—scanning mirror-lens combination described earlier.

Sampling at different locations can also be achieved by moving the material to be sampled instead of moving the sampling locations with respect to the instrument. A dosage unit could be rotated or tumbled, for example, in front of a single-point detector. A x-y stage could also be moved randomly with respect to a detector.

Sampling can also take place from different vantage points. Different sample locations could be acquired from opposite sides of a tablet, for example, by different detectors, optical conduits, mirrors, or other suitable arrangements.

Figure 5:
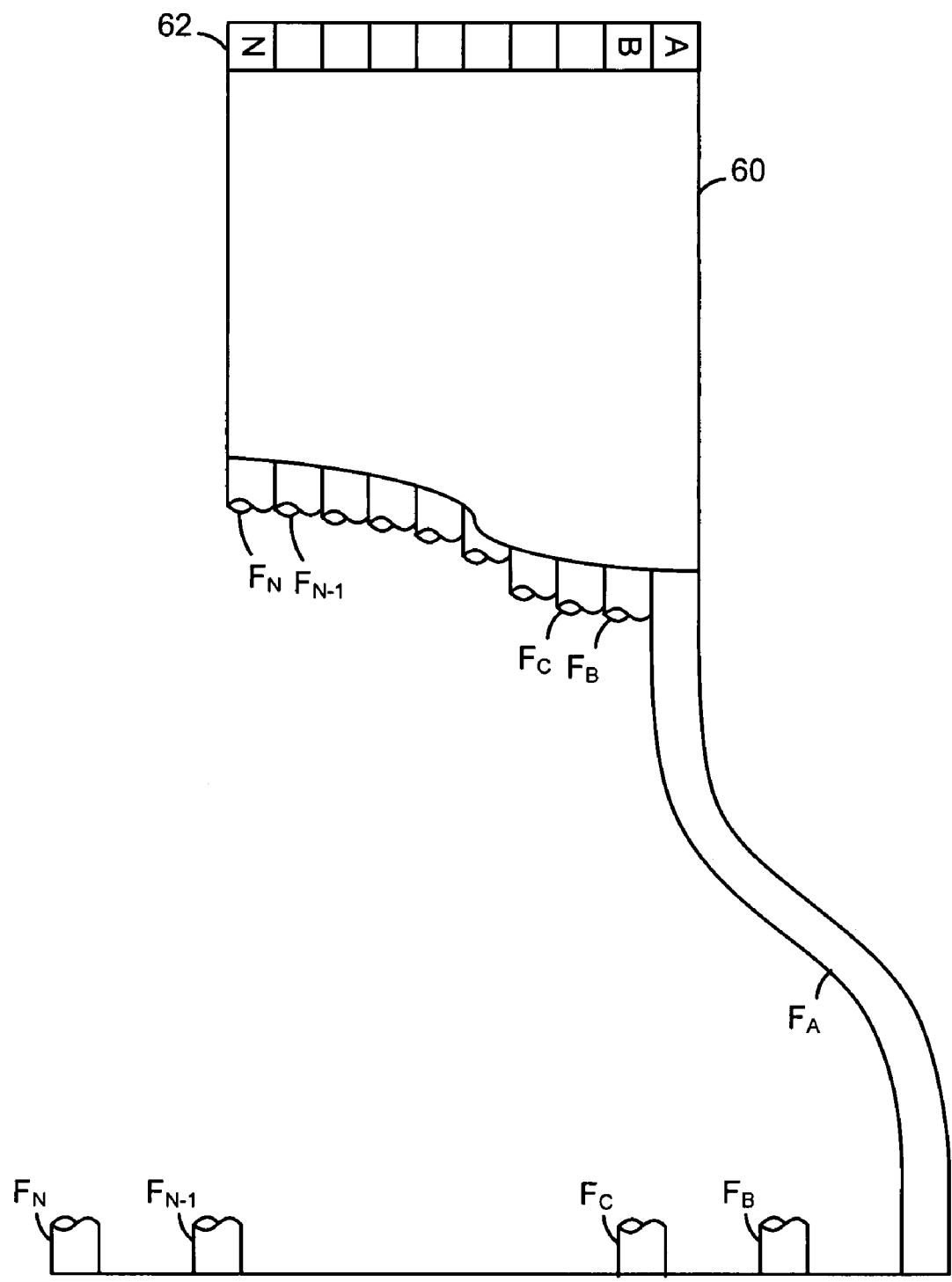
FIG. 5 is a diagram of a fiber-bundle implementation of a detector element for the system of FIG. 1.

Referring to FIG. 5, another possible implementation of the sampling detector 20 employs an optical fiber bundle 60, with one end positioned next to a relatively small one- or two-dimensional array. The fibers from the other end of the bundle are spread out and positioned to acquire micro-samples from different locations in the blend. Broad area illumination could also be imaged onto the face of a fiber bundle which is round at one end and linear on the other end. For FT illumination the linear end would be imaged directly onto a diode array. For unmodulated illumination the linear end would form the entrance slit of an imaging spectrograph, and a 2-D array detector would collect the spectral and spatial information on different axes.

The sequencing of acquisitions can take place in any suitable manner. It can use a computer program or dedicated circuit or a combination of the two. It can also use other types of principles, such as optical, mechanical, or electro-optical principles. In the embodiment of FIG. 1, for example, the sequencer can receive a position signal from a shaft encoder on the blender motor to synchronize macro acquisitions with the position of the blender. In some situations, the sequencer functions may even be impossible to isolate from the sampling detector. A sampling detector that is designed with a suitable mechanical resonant frequency, for example, can be allowed to simply run free in the acquisition of micro-samples.

Referring to FIG. 6, as the mixing process proceeds, each set of micro-samples exhibits a different set of statistical properties. Typically, the standard deviation of the acquired spectra will narrow as the mixture becomes more uniform. The mean will also tend to shift, reflecting the distribution of all of the mixture components throughout the vessel.

The statistical techniques performed by the statistical processor 24 can be applied to raw spectral data, or derived values, such as chemical or physical properties. The statistical properties can be computed as the micro-samples are being acquired and/or after a full run.

Referring to FIG. 7, the evolution of one or more of the statistical properties can be determined to characterize the process. This information can then be displayed to the user, and it can also be used in a variety of other ways, such as to decide whether a mixture has reached an end point. As shown in FIG. 8, the statistical information from the micro-macro-sampling process can also be presented as overall bulk distribution statistics.

Figure 9:
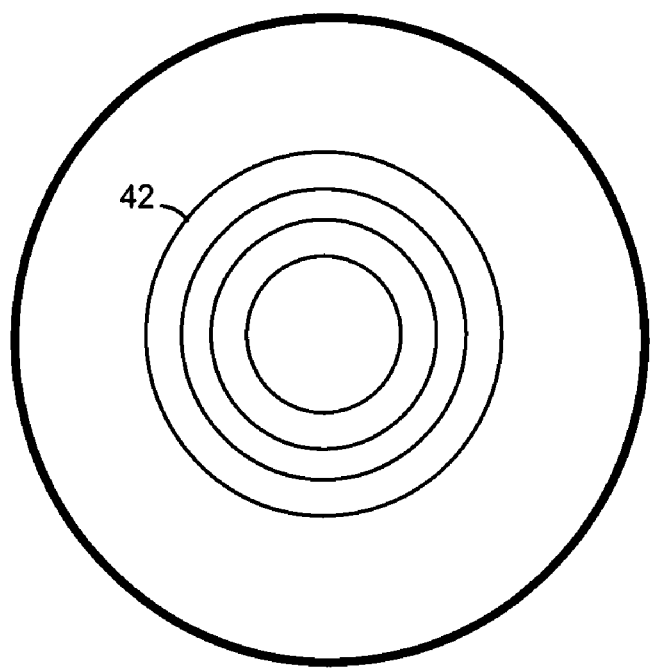
FIG. 9 is a first illustrative sampling map for a system employing differently sized sample locations.

Referring to FIG. 9, the system can also acquire samples of differently sized micro locations. These micro locations can be concentric or otherwise overlapping, or they can be distributed around the sample.

Figure 10:
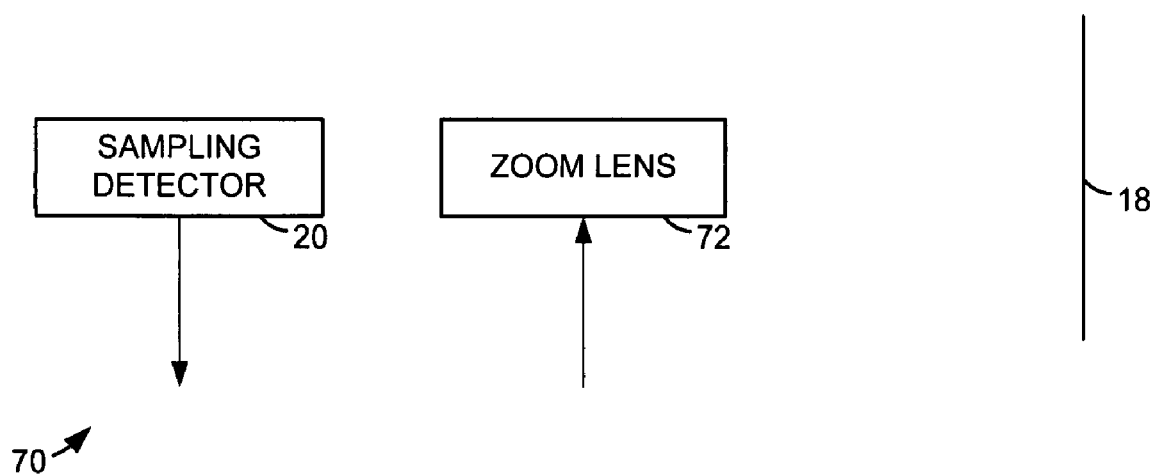
FIG. 10 is a partial system diagram for an embodiment of the system that can produce sampling maps according to FIG. 9.

Referring to FIG. 10, one approach to acquiring samples from differently sized micro locations is to introduce an electrically controlled zoom lens between the detector 20 and window 18 or other sample target. In this embodiment, the modified system 70 alternates between acquiring a measurement and adjusting the magnification of the zoom lens to assemble a series of measurements corresponding to differently sized micro locations. Such a series could also be obtained in a variety of other ways. For example, the system could illuminate different amounts of the sample, actuate different numbers of mirrors in a mirror array, and/or acquire light from different numbers of fibers.

Acquiring measurements from differently sized locations can provide additional information about the distribution of particles in a sample. Measurements over large areas will generally be representative of a number of different particles and will therefore reflect an average for these particles. Measurements over areas that are similar in size to individual particles will tend to reflect a single species. As size decreases in a series of measurements, therefore, the acquired spectrum will generally evolve from showing a mixture of species to showing just spectral features corresponding to an individual species. Chemometric analysis techniques can also be applied to the series of measurements to derive more detailed information about particle size and relative ingredient concentrations.

The techniques described above can also be applied to determine the uniformity of a pharmaceutical compound that is in the form of dosage units. This approach can allow the system to acquire information about the uniformity of the mixture within each unit and/or across a lot of units, and the sampling can take place before or after the dosage units are packaged in transparent blister packs. Relevant techniques for this type of measurement can be found in U.S. Pat. No. 6,690,464, which is herein incorporated by reference. Staining techniques may also help to enhance the information received from some experimental runs. These techniques are described in U.S. application Ser. No. 11/265,796, published under WO2006044861, and herein incorporated by reference. Moreover, while the techniques presented above have been developed for use in the characterization of pharmaceuticals, they may also be applicable to other types of products, such as cosmetics or nutritional supplements. Coated goods, drug delivery systems, medical devices, and composite materials may also be inspected using systems according to the invention.

The present invention has now been described in connection with a number of specific embodiments thereof. However, numerous modifications which are contemplated as falling within the scope of the present invention should now be apparent to those skilled in the art. It is therefore intended that the scope of the present invention be limited only by the scope of the claims appended hereto. In addition, the order of presentation of the claims should not be construed to limit the scope of any particular term in the claims.

What is claimed is:

1. A spectroscopic method for monitoring heterogeneity of a sample, comprising: acquiring a plurality of sampled spectroscopic measurements distributed over a range of different micro locations in a macro-sample of the sample,
    repeating the step of acquiring for each of a plurality of micro-locations in each of further macro-samples of the sample, and
    deriving from the sampled spectroscopic measurements acquired in the steps of acquiring a statistical measure of chemical heterogeneity.

2. The method of claim 1 wherein the steps of acquiring are performed for a pharmaceutical mixture during a blending process.

3. The method of claim 2 wherein the blending process is intermittent and wherein each of the macro-samples is an exposed area of the pharmaceutical mixture that is presented during a pause in the blending process.

4. The method of claim 1 wherein the steps of acquiring are performed for a plurality of pharmaceutical dosage units.

5. The method of claim 4 wherein each of the steps of acquiring is performed for a different one of the plurality of dosage units.

6. The method of claim 1 wherein the step of acquiring operates on light brought from micro-samples through a plurality of optical channels.

7. The method of claim 6 wherein the optical channels are optical fibers.

8. The method of claim 1 wherein the step of acquiring operates on light brought from the micro-locations to a set of detectors.

9. The method of claim 1 wherein the steps of acquiring are performed using at least one moving mirror.

10. The method of claim 1 wherein the size of the micro-samples is on the order of the milled ingredient size for a pharmaceutical mixture.

11. The method of claim 1 wherein the size of the micro-samples is on the order of the domain sizes of individual species in a pharmaceutical mixture.

12. The method of claim 1 wherein the size of the micro-samples is on the order of 10 microns.

13. The method of claim 1 wherein the size of the micro-samples is on the order of 125 microns.

14. The method of claim 1 wherein the macro-samples are taken for a part of the surface area of the sample.

15. The method of claim 1 wherein the sampled spectroscopic measurements are acquired from different vantage points.

16. The method of claim 1 wherein the sample is moved relative to a detector to cause the sampled spectroscopic measurements to be acquired from different locations.

17. The method of claim 1 wherein the steps of acquiring and repeating employ differently sized micro locations.

18. The method of claim 17 wherein the differently sized micro locations are concentric.

19. A spectroscopic apparatus for monitoring heterogeneity of a sample, comprising: means for acquiring sampled spectroscopic measurements distributed over a range of different micro locations in a macro-sample of the sample, means for causing the sampling detector to repeatedly acquire samples for each of a plurality of micro-locations in each of a plurality of macro-samples of the sample, and means for deriving from the sampled spectroscopic measurements a statistical measure of chemical heterogeneity.

20. A spectroscopic method for monitoring heterogeneity of a sample, comprising: acquiring a first sampled spectroscopic measurement of a first size in a sample of the sample, acquiring a second sampled spectroscopic measurement of a second size in a sample of the sample, wherein the first and second measurements are of the same type, and deriving from the sampled spectroscopic measurements acquired in the steps of acquiring a measure of chemical heterogeneity.

21. The method of claim 20 further including a step of adjusting a lens to adjust the size of the sampled micro location.

22. The method of claim 20 wherein the step of acquiring a first sample and the step of acquiring a second sample acquire samples that are concentric.

23. The method of claim 20 wherein the step of acquiring a first sample and the step of acquiring a second sample are performed for a pharmaceutical mixture.

24. A spectroscopic apparatus for monitoring heterogeneity of a sample, comprising: one or more sampling detectors operative to acquire spectroscopic measurements from the sample, means for causing the one or more sampling detectors to acquire a first sampled spectroscopic measurement of a first size in a sample of the sample, and a second sampled spectroscopic measurement of a second size in a sample of the sample, wherein the first and second measurements are of the same type, and a spectral processor operative to derive from the sampled spectroscopic measurements a statistical measure of chemical heterogeneity.

25. The method of claim 24 wherein the means for causing includes an adjustable lens.

26. A spectroscopic apparatus for monitoring heterogeneity of a sample, comprising: a sampling detector operative to acquire sampled spectroscopic measurements distributed over a range of different micro locations in a macro-sample of the sample, a sequencer operative to cause the sampling detector to repeatedly acquire samples for each of a plurality of micro-locations in each of a plurality of macro-samples of the sample, and a spectral processor operative to derive from the sampled spectroscopic measurements a statistical measure of chemical heterogeneity.

* * * * *